United States Patent [19]

Kojima et al.

[11] Patent Number: 4,931,291

[45] Date of Patent: * Jun. 5, 1990

[54] FEEDS FOR LARVAE OF CRUSTACEONS AND SHELLFISH

[75] Inventors: Eiji Kojima, Kanagawa; Kiyohiro Kitagawa, Chiba; Akira Seto, Kanagawa, all of Japan

[73] Assignee: The Nisshin Oil Mills, Ltd., Tokyo, Japan

[*] Notice: The portion of the term of this patent subsequent to Mar. 6, 2007 has been disclaimed.

[21] Appl. No.: 220,387

[22] Filed: Jul. 12, 1988

Related U.S. Application Data

[63] Continuation of Ser. No. 62,248, Jun. 15, 1987, abandoned.

[30] Foreign Application Priority Data

Jun. 24, 1986 [JP] Japan ................................ 61-147279

[51] Int. Cl.$^5$ ............................................... A23K 1/10
[52] U.S. Cl. ......................................... 426/2; 426/58; 426/59; 426/385; 426/519; 426/646
[58] Field of Search ................... 426/635, 1, 2, 58, 59, 426/60, 646, 385, 519

[56] References Cited

FOREIGN PATENT DOCUMENTS 57-150379 of 1982 Japan .................................. 426/643

OTHER PUBLICATIONS

Watanabe et al., Relationship between dietary value of Brine Shrimp Artemia Salina and their content of W 3 highly unsaturated fatty acid "Bull. of the Japanese Soc. of Scientific Fisheries", vol. 46, pp. 35–41 (1980).
Dunmill et al., "Protein Extraction & Recovery from Microbial Cells" Single Cell Protein II MIT Press. (1976), pp. 179–207.
*Bulletin of the Japanese Society of Scientific Fisheries*, vol. 44, No. 10, pp. 1109–1114, (1978), "Nutritional Quality of Rotifer Brachionus Plicatilis as a Living Feed from the Viewpoint of Essential Fatty Acids for Fish", T. Watanabe, C. Kitajima, T. Arakawa, K. Fukusho and S. Fujita.
*Bulletin of the Japanese Society of Scientific Fisheries*, vol. 45, No. 8, pp. 955–959, (1979), "Development of a New Yeast as a Culture Medium for Living Feeds Used in the Production of Fish Seed":, O. Imada, Y. Kageyama, T. Watanabe, C. Kitajima, S. Fujita and Y. Yone.
*Bulletin of the Japanese Society of Scientific Fisheries*, vol. 45, No. 7, pp. 883–889, (1979), "Relationship between the Dietary Value of Rotifers Brachionus plicatilis and their content of W3 Highly Unsaturated Fatty Acids", T. Watanabe, F. Dowa, C. Kitajima, S. Fujita and Y. Yone.
*Oil Chemistry*, vol. 31, No. 2, pp. 77–90, (1982), "Nutritional Quality of Live Feeds Used in the Seed Production of Fish from the View–Point of Essential Fatty Acids", T. Watanabe.
Lecture Briefings, p. 143, 50th Conference of Japan Plant Society.

*Primary Examiner*—R. B. Penland
*Attorney, Agent, or Firm*—Albert L. Jeffers; Lawrence A. Steward

[57] ABSTRACT

Feeds comprising unicellular algaes whose cell wall are disrupted are provided as the feeds for larvae of crustaceans and shellfishes to be cultivated. With such feeds, it is possible to achieve the rates of survival and growth equivalent to, or higher than, those achieved with untreated diatom.

10 Claims, No Drawings

FEEDS FOR LARVAE OF CRUSTACEONS AND SHELLFISH

This is a continuation of application Ser. No. 026,248, filed Jun. 15, 1987 now abandoned.

BACKGROUND OF THE INVENTION

1. Field of the Invention

The present invention relates to a feed for larvae of crustaceans (except for artemia) such as lobsters, crabs, earshells (awabi) and sea urchins and shellfishes which are important marine resources.

2. Related Art Statement

All over the world inclusive of Japan, culture fishery and breeding have showed marked technological advancement with the yield increasing steadily year by year.

In culture fishery and cultivation fields, however, a number of factors concerning the feeding and breeding of fry and small fishes at the initial stage considered of the most importance are still unclarified, partly because they are very minute individuals. Considerable difficulty involved in the production of feed formulations accommodative to minute individuals stands in the way of any fruitful studies of nutritional and other requirements.

For the reasons as mentioned above, the breeding at this state often relies upon long experiences and the so-called "the sixth sense". As a matter of course, this results in lowerings of the yield and noticeable variations in the annual yield.

For instance, floating and deposited diatoms belonging to Skeletonema and Cheatoceros are now widely used as the optimum feeds for natantia peneus larvae (of the zoeal and mysis stages). Difficulties are encountered in the stable cultivation of diatoms, because they grow at a low rate, are affected by weather, and tend to be easily contaminated by other organisms.

Substituent feed formulations for diatoms have recently been studied. However, it is difficult to triturate and regulate such feed formulations to a size of 5 to 50 microns that is the size of diatoms. Another disadvantage of such feed formulations is that, even though they are regulated in size, their particles are so fine that their contents are readily soluble in breeding water, leading to not only ready losses of nutritive value but also marked contamination of the breeding water.

Further, for the production of seedlings for shellfishes such as *Pleurotomaria nordotis, Temnopleuroida pseudocentrotus, Pleurotomaria sulculus* and *Ostracea crassoster*, diatoms are used as the feeds at their larval stage. However, since the production of diatoms is uncertain in itself as mentioned above, there are raised problems of low yield rate in breeding of larvae and deviation in the yield.

Still further, such shellfishes take in floating diatoms and, then, deposited diatoms over a period of several months. However, it has been found that the production of such deposited diatoms requires much more labor and time, and undergoes much larger weather influences, than does the production of floating diatoms.

SUMMARY OF THE INVENTION

An object of the present invention is to provide a feed for larvae of crustaceans (except for artemia) and shellfishes, which can be substituted for diatoms.

Another object of the present invention is to further improve the feeding efficiency of the conventional diatoms.

The present invention has been accomplished on the basis of the findings that the above-mentioned problems are solved by feeds obtained by applying various cell wall-disrupting treatments to unicellular algaes.

More specifically, the present invention provides a feed for larvae of crustaceans (except for artemia) and shellfishes, which comprises unicellular algaes having the cell walls disrupted.

DETAILED DESCRIPTION OF THE INVENTION

The "unicellular algaes" referred to in this disclosure refer to fresh water and seawater ones, and mainly include fresh water and seawater chlorella, diatoms and the blue-green algaes.

The term "fresh water chlorella" used herein refers to those usually broken down into *Chlorella vulgaris, Chlorella ellipsoidea, Chlorella pyrenoidosa, Chlorella parasitica, Chlorella conglomerata, Chlorella variegata, Chlorella autotrophica, Chlorella mutabilis, Chlorella nocturna, Chlorella photophila* and the like.

The term "seawater chlorella" has been taken as referring to those used for the cultivation of rotisers in the fishery cultivation field and called *Chlorella minutissima*, and the like [see "Bulletin of the Japanese Society of Scientific Fisheries", Vol. 44, No. 10, pp. 1109–1114 (1978); Vol. 45, No. 7, pp. 883–889 (1979); and Vol. 45, No. 8, pp. 955–959 (1979) and "Oil Chemistry", Vol. 31, No. 2, pp. 77–90 (1982))]. Recently, however, it has been made public that the seawater chlorella belongs to Nannochloropsis (see Lecture Briefings, p. 143, in the 50th conference of Japan Plant Society). Thus, the classification system of the seawater chlorella has not definitely established as yet. For reasons of convenience, the present disclosure follows the foregoing term as used in the fishery cultivation field.

The "diatoms" used herein refer to those classified into *Cheatoceros glacilis, Cheatoceros simplex, Skeletonema costatum* and the like.

The disruption of cell walls is carried out by spray dry treatment, ultrasonic treatment, triturating treatment, treatment with an enzyme for the lysis of cell walls and other treatments. For all the treatments, the wet cells are used, obtained by washing several times unicellular algaes after cultivation.

The spray dry treatment is carried out with a wet cell solution having its solid content regulated to 2 to 10%, preferably 3 to 5% at an air blow temperature of 140° to 160° C. and an air discharge temperature of 100° to 130° C.

The ultrasonic treatment is effected with a commercially available ultrasonic generator at a solid content similar to the aforesaid one, while applying cooling so as to maintain a temperature of up to 60° C.

For the triturating treatment, sea sand, glass beads and the like are mixed with a wet cell solution, which is then treated in a triturator such as a homoblender, thereby disrupting the cell walls.

The cell wall-lysis enzymes to be used include protease (PAPAIN manufactured by Amano Seiyaku K. K., etc.), cellulase (Onozuka Cellulase R10 manufactured by Yakult K. K., Meicelase manufactured by Meiji Seika K. K., etc.), hemicellulase (Macerozyme manufactured by Yakult K. K., etc.), pectinase (Pectoriase manufactured by Seishin Seiyaku K. K., etc.) and the like, which may be used alone or in combination. In the present invention, however, it is to be noted that any limitation is not imposed upon the type of the enzymes to be used. It is also to be noted that the enzymatic treatment conditions (pH, temperature, time and like factors) vary with the type of the enzymes used, and should preferably be chosen with the optimum conditions of the enzyme used in mind.

If required, an amount of water is added to the unicellular algaes whose cell walls have been disrupted by any one of the aforesaid treatments. Thereafter, phospholipid such as soybean lecithin, sterol such as cholesterol and phytosterol, glycolipid or dicetyl phosphate is added to the unicellular algaes in an amount of about 1 to 50%, preferably about 3 to 10% on the dry basis for uniform dispersion. In this manner, a more stable dispersion is obtained.

If the spray dry treatment is used for the disruption of cell walls, it is desired that the following procedures be applied. A dry product of such unicellular algae is dispersed to a dry matter content of about 5 to 15% in water, followed by forced dispersion with a high-pressure homogenizer (operated at a discharge pressure of 300~500 kg/cm$^2$) or a polytron homogenizer. An aggregation of several hundred-chlorella cells before that forced dispersion are divided thereby into individual cells or agglomerate of several cells, which provide them easily edible by larvae of crustaceans and shellfishes.

The thus obtained feeds may be bonded together and formed into a plate or film-shaped product with various high-molecular materials, which may be a replacement to the deposited diatoms. The high-molecular materials to be used include alginic acid, polysaccharides such as agar, Koniaku mannan and starch, proteins such as soybean protein and egg albumin, synthetic high molecular materials such as polyacrylamide and carboxymethylcellulose, and the like.

The feeds of the present invention can be used for the production of larvae for prawns, crabs, awabi, sea urchins, haliotis and oysters.

EXAMPLES

EXAMPLE 1

Live dispersions (having a wet mass of 10 weight %) of diatoms (*Skeletonema costatum*), seawater chlorella (*Chlorella minutissima*) and fresh water chlorella (*Chlorella vulgaris*) are (1) untreated (for control), or (2) triturated by a polytron homogenizer, (3) treated by ultrasonics and (4) enzymatically treated with cellulase.

For the triturating treatment, a small amount of sea sand was added to the live dispersion, and the resulting product was treated at a temperature of up to 50° C. for 5 to 10 minutes in a polytron homogenizer (3,000–10,000 rpm). The ultrasonic treatment was carried out at 20 KHz for 30 minutes with commercially available ultrasonic pulverizer (Tosho Electric K. K. ), while cooling was applied to maintain a liquid temperature of up to 50° C. For the enzymatic treatment, three types of cellulase (Cellcrast manufactured by Nobo K. K., Cellulase A-3 manufactured by Amano Seiyaku K. K., and Meicellulase manufactured by Meiji Seika K. K.) were added to the dispersions in the respective amounts of 10 g/l, 5 g/l and 5 g/l for 4 hour-reaction at 45° C. During the reaction, the pH of each dispersion was controlled to about 6. About the reaction, the pH of each dispersion was controlled to about 6. After the reaction had been completed, the reaction products were heated to 80° C. for enzyme deactivation to obtain experimental feeds.

With the aforesaid respective feeds, *natantia peneus* nauprius were bred in the following manner. 400,000 individuals of *natantia peneus* nauprius were poured into four 1-ton water tanks, each at a density of 100 individuals per liter. From just before the metamorphase of nauprius into zoea, the respective feeds were fed in an amount of 5 g/ton a day on the basis of the weight of wet cells. Other breeding conditions followed those used in the ordinary method. The survival rate with time and the state of growth and metamorphase are set out in Table 1.

TABLE 1

| | | Changes in Length (mm) and Survival Rate (%) of Natantia peneus | | | | |
|---|---|---|---|---|---|---|
| | | Days after metamorphase to zoea | | | | |
| Foods | | 1 | 2 | 3 | 4 | 5 |
| Diatoms | Control | 1.09 (78) | 1.40 (69) | 1.95 (50) | 2.26 (46) | Mysis (45) |
| | Trituration | 1.09 (80) | 1.42 (74) | 1.89 (56) | 2.30 (50) | Mysis (48) |
| | Ultrasonic | 1.10 (82) | 1.50 (73) | 2.01 (54) | 2.35 (46) | Mysis (42) |
| | Cellulase | 1.12 (85) | 1.51 (76) | 2.12 (61) | Mysis (60) | 3.18 (55) |
| Seawater Chlorella | Control | 1.02 (60) | 1.40 (30) | 1.65 (25) | 1.78 (10) | 1.85 (3) |
| | Trituration | 1.09 (82) | 1.43 (74) | 1.95 (56) | 2.31 (49) | Mysis (46) |
| | Ultrasonic | 1.09 (80) | 1.54 (75) | 2.10 (62) | 2.34 (52) | Mysis (46) |
| | Cellulase | 1.10 (84) | 1.49 (77) | 2.25 (68) | Mysis (63) | 3.31 (58) |
| Fresh Water Chlorella | Control | 1.03 (65) | 1.38 (28) | 1.60 (25) | 1.79 (12) | 1.89 (2) |
| | Trituration | 1.07 (80) | 1.38 (70) | 1.71 (50) | 1.92 (42) | 2.10 (35) |
| | Ultrasonic | 1.07 (78) | 1.46 (68) | 1.91 (51) | 2.10 (46) | Mysis (40) |
| | Cellulase | 1.09 (81) | 1.46 (69) | 1.93 (59) | 2.15 (48) | Mysis (41) |

Bracketed figures denote the rate of survival

From Table 1, it is noted that the feeding efficiency of the diatoms is increased by the enzymatic treatment with cellulase, although the diatoms may sufficiently be used as such due to their relatively high original digestibility. On the other hand, the seawater and fresh water chlorella was hardly digested, while in the live form, thus resulting in a sharp lowering of the survival rate. However, the growth and survival rates of these larvae were considerably improved by the treatments according to the present invention.

EXAMPLE 2

Live dispersions (having a wet mass content of 10% by weight) of seawater chlorella (*Chlorella minutissima*) and fresh water chlorella (*Chlorella ellipsoidea*) are treated with cellulase under the same conditions as in Ex. 1, and are thereafter spray-dried at an air feed temperature of 150° C. and an air discharge temperature of 110° C. The obtained dry powders are again hydrated to a solid mass content of 5%, and are then dispersed into lumps comprising one to several cells by means of a high-pressure homogenizer (operated at a discharge pressure of 500 kg/cm$^2$). With the thus obtained dispersions used as the feeds, the breeding experiment of *Temnopleuroida pseudocentrotus* was carried out in the following manner. *Temnopleuroida pseudocentrotus* eggs were poured in three 500-liter water tanks each at a density of 800,000 eggs/ton, and the respective feeds were added, while the temperature of water was maintained at 20°±1.0° C. In the meantime, the feeds were added at a density of 50,000 cells/ml as measured just after the addition, and the rate of growth was observed with time.

As a result, the rate of growth was equal to, or higher than, that achieved with diatoms, as shown in Table 2.

TABLE 2

Relationship between the Days required for *Temnopleuroid pseudocentrotus* to reach the respective growth stages and the feeds supplied

| Feeds | Growth Stage (Brachial Stage) | | |
|---|---|---|---|
| | 4 → 6 | 6 → 8 | 8 ↓ Metamorphic Desposition |
| Diatoms (*C. gracillis*) | 3 days | 9 | 14 |
| Untreated Seawater Chlorella | 7 (No growth found afterwords) | — | — |
| Untreated Fresh Water Chlorella | 6 | 15 (No growth found afterwords) | — |
| Seawater Chlorella Whose Cell Walls have been disrupted | 3 | 8 | 13 |
| Fresh Water Chlorella Whose Cell Walls have been Disrupted | 4 | 12 | 17 |

EXAMPLE 3

Added to the solutions of the seawater and fresh water chlorella having the cell walls disrupted, which are prepared according to Ex. 2, is sodium aliginate in an amount of 3% to obtain pasty products. The products are applied on the surface of a corrugated plate formed of plastics, which is then immersed in a 5% calcium chloride solution to form gel. After sufficient removal of water, freeze-drying of the gel gave a replacement to the deposited diatoms. Use of such a replacement for the breeding of fry of *pleurotomaria nordotis* indicated that a growth rate almost similar to that achieved with ordinary deposited diatoms was obtained.

EXAMPLE 4

Added to 100 parts of the dispersion of seawater chlorella (having a wet mass content of 10% by weight) whose cell walls were disrupted were 1 part of soybean phospholipid, 0.2 parts of cholesterol and 0.05 parts of dicetyl phosphate, followed by dispersion with a polytron homogenizer. The obtained dispersion was found to have the properties of being hard to agglutinate even after storage over an extended period, as compared with one not containing any phospholipid, cholesterol and dicetyl phosphate. It did not also lose its nutritional effect.

According to the present invention, it is possible to stably produce the larvae of crustaceans and shellfishes, making use of easily cultivatable chlorella.

If diatoms are treated in accordance with the present invention, then their feeding efficiency is further improved.

What is claimed is:

1. A process for breeding larvae of Crustaceans, except for Artemias, and shellfishes which comprises feeding to the larvae unicellular algae having its cell wall disrupted, said unicellular algae being selected from the group consisting of fresh water Chlorella, seawater Chlorella, diatoms and blue-green algae, wherein the cell walls of said unicellular algae are disrupted by any one or more of spray dry treatment, ultrasonic treatment, triturating treatment and cell wall-lysis enzymatic treatment and whereby the growth rate and survival rate of the larvae are substantially improved.

2. The process as claimed in claim 1 wherein the disruption of the cell walls of said unicellular algae is carried out with the spray dry treatment, and after said spray dry treatment the cells are hydrated and forcedly dispersed in the form of individual cells or agglomerate of several cells by means of a high-pressure homogenizer or a polytron homogenizer.

3. The process as claimed in claim 1 wherein at least one member selected from the class consisting of phospholipids, sterols, glycolipids and dicetyl phosphate is added to and uniformly dispersed in said unicellular algae, the cell walls of which have been disrupted.

4. The process as claimed in claim 1 wherein said unicellular algaes, the cell walls of which have been disrupted, are bonded together into a plate or film shape with a natural high molecular weight material.

5. The process as claimed in claim 1 wherein said unicellular algaes, the cell walls of which have been disrupted, are bonded together into a plate or film shape with a synthetic high molecular weight material.

6. The process as claimed in claim 1 wherein a natural high molecular weight material is added to said unicellular algaes, the cell walls of which have been disrupted, to obtain a pasty product, and said pasty product is applied on the surface of a substrate for gelling, followed by freeze drying.

7. The process as claimed in claim 1 wherein a synthetic high molecular material is added to said unicellular algaes, the cell walls of which have been disrupted, to obtain a pasty product, and said pasty product is applied on the surface of a substrate for gelling, followed by freeze drying.

8. The process as claimed in claim 1 wherein said seawater Chlorella is *Chlorella minutissima*.

9. The process as claimed in claim 1 wherein said fresh water Chlorella is at least one selected from the group consisting of *Chlorella vulgaris, Chlorella ellipsoidea, Chlorella pyrenoidosa, Chlorella parasitica, Chlorella conglomerata, Chlorella variegata, Chlorella autotrophica, Chlorella mutabilis, Chlorella nocturna* and *Chlorella photophila*.

10. The process as claimed in claim 1 wherein said diatoms are at least one selected from the group consisting of *Cheatoceros glacillis, Cheatoceros simplex* and *Skeletonema costatum*.

* * * * *